US010874708B2

(12) United States Patent
Jiménez del Rio et al.

(10) Patent No.: US 10,874,708 B2
(45) Date of Patent: Dec. 29, 2020

(54) COMPOSITIONS FOR REDUCING APPETITE AND CRAVING, INCREASING SATIETY, ENHANCING MOOD, AND REDUCING STRESS

(71) Applicant: NEKTIUM PHARMA, S.L., Aguimes (ES)

(72) Inventors: Miguel Jiménez del Rio, Telde (ES); Julia C. Wiebe, Las Palmas de GC (ES); Laura Lopez-Rios, Las Palmas de GC (ES); Tanausu Vega-Morales, Las Palmas de GC (ES); Ruben Perez-Machin, Las Palmas de GC (ES); Alvaro Sanchez-Rodriguez, Las Palmas de GC (ES); Carlos J. Mateos, Las Palmas de GC (ES); Nigel Peter Gericke, Cape Town (ZA)

(73) Assignee: NEKTIUM PHARMA, S.L., Las Palmas (ES)

( * ) Notice: Subject to any disclaimer, the term of this patent is extended or adjusted under 35 U.S.C. 154(b) by 309 days.

(21) Appl. No.: 15/402,886

(22) Filed: Jan. 10, 2017

(65) Prior Publication Data
US 2018/0193400 A1    Jul. 12, 2018

(51) Int. Cl.
| | |
|---|---|
| *A61K 36/8905* | (2006.01) |
| *A61K 31/352* | (2006.01) |
| *A61K 36/22* | (2006.01) |
| *A23L 33/105* | (2016.01) |
| *A61P 25/24* | (2006.01) |
| *A61K 31/7048* | (2006.01) |
| *A61P 3/04* | (2006.01) |
| *A61P 25/34* | (2006.01) |
| *A61P 25/32* | (2006.01) |

(52) U.S. Cl.
CPC ........ *A61K 36/8905* (2013.01); *A23L 33/105* (2016.08); *A61K 31/352* (2013.01); *A61K 31/7048* (2013.01); *A61K 36/22* (2013.01); *A61P 3/04* (2018.01); *A61P 25/24* (2018.01); *A61P 25/32* (2018.01); *A61P 25/34* (2018.01); *A61K 2236/33* (2013.01); *A61K 2236/333* (2013.01)

(58) Field of Classification Search
None
See application file for complete search history.

(56) References Cited

U.S. PATENT DOCUMENTS

| | | | |
|---|---|---|---|
| 4,436,732 A | 3/1984 | Vichkanova | |
| 4,518,592 A | 5/1985 | Rusakova | |
| 5,900,267 A | 5/1999 | Monros | |
| 5,985,282 A | 11/1999 | Haveson | |
| 6,613,797 B2 | 9/2003 | Winter | |
| 7,854,948 B2 | 12/2010 | Slimak | |
| 8,277,850 B2 | 10/2012 | Paufique | |
| 8,334,267 B2 | 12/2012 | Teng | |
| 9,163,312 B2 | 10/2015 | Woods | |
| 2011/0046077 A1 | 2/2011 | Talamond et al. | |
| 2014/0220220 A1 | 8/2014 | Arday et al. | |

FOREIGN PATENT DOCUMENTS

| | | |
|---|---|---|
| CN | 101003558 A | 7/2007 |
| CN | 101269161 A | 9/2008 |
| CN | 101270230 A | 9/2008 |
| CN | 101731710 A | 6/2010 |
| CN | 101732360 A | 6/2010 |
| CN | 101848922 A | 9/2010 |
| CN | 102920696 A | 2/2013 |
| CN | 103191141 A | 7/2013 |
| CN | 104557892 A | 4/2015 |
| EP | 2397039 A1 | 12/2011 |
| EP | 2 444 094 A1 | 4/2012 |
| RU | 2176516 C1 | 12/2001 |
| RU | 2197259 C1 | 1/2003 |
| WO | 2008/061480 A1 | 5/2008 |
| WO | 2018/025080 A2 | 2/2018 |

OTHER PUBLICATIONS

Bamishaiye (African Journal of Food, Agriculture, Nutrition, and Development (2011), vol. 11, No. 5, pp. 5158-5170).*
Ding (Diabetologia (2014), vol. 57, pp. 2145-2154).*
"Nutrition and Health Benefits of Tiger Nuts (Yellow nutgrass, Chufa, *Cyperus esculentus*)", By Inform Africa (http://www.informafrica.com/author/informafrica/) on May 10, 2012—1 Comment (http://www.informafrica.com/healthafrica/nutritionandhealthbenefitsoftigernutsyellownutgrasschufacyperusesculentus/#comments), Feb. 16, 2016.
Dimitrov, et al., "Acute Toxicity, Antidepressive and MAO Inhibitory Activity of Mangiferin Isolated From Hypericum Aucheri", Biotechnol. & Biotechnol. Eq. 2011, 25(4), 2668-2671.
Dimpfel, "Drug Discovery and Translational Medicine—Neurophysiological Techniques Provide a Holistic Approach to Saving Animals", Freienbrink Herstellung und Verlag. ISBN: 978-3-7386-7039-4, pp. 47-54 (2015).

(Continued)

*Primary Examiner* — Susan Hoffman
(74) *Attorney, Agent, or Firm* — Kramer Amado, P.C.

(57) ABSTRACT

A method for enhancing at least one of craving-reduction, mood improvement, avoidance of depression, prevention of weight gain post weight-loss from dieting, reduction of negative side effects produced by anti-appetite drugs and smoke-cessation and promotion of healthy ageing in a person in need thereof, comprising administering a composition to said person, said composition comprising:
a) an effective amount of an extract of *Cyperus esculentus* peel, *Cyperus esculentus* rhizomes, or a combination thereof;
b) an effective amount of mangiferin, norathyriol, or an extract comprising mangiferin or norathyriol; or
c) a synergistic combination of (a) and (b).
The composition may comprise a third active ingredient in combination with the *Cyperus esculentus* extract and mangiferin or norathyriol.

17 Claims, 2 Drawing Sheets

(56) References Cited

OTHER PUBLICATIONS

Karababa, "Chemical Composition and Technological Evaluation fo Chufa Tuber (*Cyperus esculentus* L.)", GIDA (2001) 26(4):243-246.

Linssen, et al., "Chufa (*Cyperus esculentus*): A New Source of Dietary Fibre", J Sci Food Agric 1989, 49, 291-296.

Macher, "Tiger Nuts and Their Amazing Weight Loss Benefits", http://gethealthygethot.com/2396/tigernutsandtheiramazingweightlossbenefits/, 2015.

Muruganandan, "Effect of mangiferin on hyperglycemia and atherogenicity in streptozotocin diabetic rats", Journal of Ethnopharmacology 97 (2005) 497-501.

Papadelis, et al., "Indicators of Sleepiness in an Ambulatory EEG Study of Night Driving", Proceedings of the 29th IEEE, EMBS Annual International Conference, New York City, USA, Aug. 30-Sep. 3, 2006, pp. 6201-6204.

Rosengarten, Jr., "Tiger Nuts", The Book of Edible Nuts, Roasted Whole Soy Flour & Soy Coffee, New York, NY, Walker and Company p. 330-332 (1984) p. 528.

Sederberg, et al., "Hippocampal and Neocortical Gamma Oscillations Predict Memory Formation in Humans", Cerebral Cortex May 2007, 17:1190-1196, Advance Access publication Jul. 10, 2006.

"Notification of Transmittal of the International Search Report and Written Opinion of the International Searching Authority, or the Declaration", for PCT/EP2018/050524 dated Mar. 14, 2018.

Devon, "Tiger Nuts: This silly-named superfood was used by humans over a million years ago", XP-002778705 Jan. 3, 2018.

Drewnowski, "Concept of a nutritious food: toward a nutrient density score 1-3", Am J Clin Nutr, 82, pp. 721-732. (2005).

O'Keefe, Jr., et al., "Cardiovascular Disease Resulting from a Diet and Lifestyle at Odds with Our Paleolithic Genome: How to Become a 21st-Century Hunter-Gatherer", Mayo Clin. Proc., 79, pp. 10-108. (2004).

\* cited by examiner

COMPOSITIONS FOR REDUCING APPETITE AND CRAVING, INCREASING SATIETY, ENHANCING MOOD, AND REDUCING STRESS

BACKGROUND

1. Technical Field

This disclosure relates generally to compositions which reduce craving for unhealthy foods, sweetened beverages and confections, nicotine-containing products, or alcohol without causing undesired physical or psychological side effects, while simultaneously enhancing mood and reducing stress.

2. Description of Related Art

This disclosure relates to a composition that reduces craving and serves as a substitute for appetite-reducing and smoking-cessation drugs. This new combination contains a plant extract of Tigernut, also known as Chufa (*Cyperus esculentus*), and an extract containing the xanthonoid compound mangiferin which might be of different origin. For example, the mangiferin-containing extract might be a Mango fruit, bark or leaf extract, Honeybush tea, or an extract of coffee leaves.

Smoking Cessation, Weight Gain and Relapse

Tobacco, containing the addictive alkaloid nicotine, is highly addictive and one of the most widely abused drugs in the world. According to the WHO worldwide about 1 billion males and 250 million females smoke. Half of them, 5.4 million per year worldwide, eventually die as a direct consequence of their tobacco addiction. The positive reinforcing effects of smoking include mild euphoria, relaxation, and improved attention and working memory, while discontinuation of smoking leads not only to nicotine withdrawal but also to depressed mood, increased stress, irritability, anxiety, and impaired memory and attention, increasing the risk for relapse to smoking. The pharmaceutical drug Rimonabant, a cannabinoid receptor CB1 inverse agonist/antagonist, decreases nicotine-taking and nicotine-seeking in rodents. Rimonabant has been shown to improve the ability of smokers to quit smoking in randomized clinical trials, but has been withdrawn from the market due to its severe psychiatric side effects and increased suicidal risk. The side effects of Rimonabant are due to the reduction in the mood-enhancing and de-stressing activities of the endocannabinoid and endogenous opiate systems, and decrease in the elevation of dopamine, induced by nicotine and food in the brain reward area, thereby leading to depression. A potential mood-enhancing pharmaceutical treatment for smoking cessation is Selegiline, a selective and irreversible monoamine oxidase B inhibitor with anti-depressive activity mainly used as neuroprotector in Parkinson's disease patients. Selegiline primarily affects dopamine levels in the brain, but cholinergic input affects nicotine-induced dopaminergic activity. Scientific evidence from 2013 suggests that targeting craving during early abstinence and adding mood management to behavioral support may improve cessation outcomes in smokers.

Smoking cessation is often accompanied by metabolic changes including increased β-cell secretion in response to glucose and fasting insulin resistance. These alterations may be associated with or contribute to the body weight gain after smoking cessation, which is reportedly a major reason why many smokers relapse after initiating smoking cessation, followed by the accompanying low mood and depression related to the missing reward response. The present combination decreases craving, increases the electroencephalographic signaling of the neurotransmitters dopamine and serotonin, thereby attenuating the reduced reward response, and simultaneously improves mood and decreases emotional stress.

Overweight and Obesity Worldwide

In 2003, worldwide more than 1 billion adults were overweight or obese. This number was doubled in 2013 reaching 2 billion individuals across all age groups and turning obesity in the leading preventable cause of death worldwide and the most serious burden for public health systems of the 21st century. In 2010, overweight and obesity caused about 3.4 million deaths worldwide, 3.9% of years of life lost, and 3.8% of disability-adjusted life-years. In 2013, the American Medical Association finally classified obesity as a disease. Both physical and psychological well-being are at risk in overweight and obese individuals due to increased risk of cardiometabolic disease and the stigma of social discrimination, particularly in the Western world. The pandemic increase in overweight and obesity in children and adults has led to widespread calls for regular monitoring of changes in overweight and obesity prevalence in all populations[1]. Overeating is the result of disequilibrium between the motivational circuits related to conditioning and reward, and circuits that control and inhibit the reward system and cognitive and affective processes implicated in the dysregulation of eating behavior.

Caloric Restriction

As opposed to the negative side effects of over-nutrition, calorie restriction is the only physiological intervention known to have a consistent and predictable effect on maintaining health and reducing the risk of disease, improving quality of life and healthspan, and retarding ageing, as demonstrated in multiple studies across diverse animal models. Many hormonal signals from peripheral tissues contribute to the regulation of energy homeostasis and food intake. These regulators including leptin, insulin, and ghrelin, modulate the orexigenic and anorexigenic neuropeptide expression in hypothalamic nuclei. A negative energy balance seems to promote the activity of specific populations of neurons in these hypothalamic nuclei that drive hunger. The anti-aging effects of caloric restriction have been explained from an evolutionary viewpoint as the adaptive response of the neuroendocrine and metabolic response systems to maximize survival during periods of food shortage. In organisms, excess energy is stored in adipose tissues as triglycerides for such survival situations. Adipose tissue has increasingly been recognized as an endocrine organ, and leptin, as secreted by adipocyte, seems to be an especially important factor for the adaptive response to fasting and neuroendocrine alterations under caloric restriction. By contrast, dysregulation of satiety signaling may have the opposite effect in that it promotes metabolic overload in tissues, ultimately leading to chronic diseases. These observations have implications for the development of anti-obesity drugs, because compounds that target satiety pathways will ultimately promote the homeostatic mechanisms that can prevent metabolic overload and therefore chronic disorders.

Obesity Drugs

The promising anorectic antiobesity drug Rimonabant was withdrawn from the market as it was associated with severe psychiatric side effects and increased suicidal risk. A stimulant drug that is also used as an appetite suppressant in weight management is Methylphenidate, the most frequently used medication for the treatment of attention-deficit/hyperactivity disorder (ADHD). In addition to suppressing appetite, a single dose of Methylphenidate decreases energy intake in the form of fat and carbohydrates in obese adolescents. Methylphenidate selectively binds to and inhibits the dopamine transporter, thus increasing brain dopamine levels, which mediate the reward value of food, shortly after oral administration. This effect underscores the importance of central dopamine signaling on eating behavior.

Regulation of Food Intake

Regions and networks of the human brain involved in eating behaviour and appetite control have been identified with neuroimaging techniques such as functional MRI, PET, electroencephalography, and magnetoencephalography. Hormones that regulate our drive to eat (e.g., leptin, insulin, and glucagon-like peptide-1) can affect brain function. The central nervous system (CNS) controls appetite and body weight regulation in a rather complicated manner. The human brain integrates internal and external inputs to modulate energy homeostasis. Currently homeostatic control by the hypothalamus is considered to be primarily responsible for controlling appetite, food intake, body weight and the development of obesity. The hypothalamic region is controlled by multiple signals coming from digestive tract, adipose tissue and pancreas in form of leptin, cholecystokinin (CCK), ghrelin, incretins, orexin, insulin, peptide YY, glucose, amino acids and fatty acids, reflecting the physiological situation of the body. The so-called reward effect, a physiological process associated with food intake, is related to the hypothalamus and several other brain regions, including the limbic region and the frontal cortex. The limbic region includes the nucleus accumbens, amygdalae and hippocampus. The neurotransmitter system of the frontal cortex responds to dopamine, serotonin, opioids, and cannabinoids, and is closely related to the reward system and the homeostasis of regulation of food intake.

Neurotransmitters

The action of the multiple neurotransmitters in relations to hunger is complex. Most of them are implicated in homeostatic and reward mechanisms, depending on the physiological situation and the affected brain areas. Brain regions with dopaminergic connections are ventral tegmental area (VTA), nucleus accumbens, dorsal striatum, frontal cortex, limbic regions, e.g., the hippocampus, amygdalae and lateral hypothalamus. While dopamine release is related to the feeling of reward as reaction to food intake, exposure to pictures representing food can also increase dopamine levels and lead to an increased desire for food.

Field Potentials and EEG Results

Neurotransmitter receptors and transporters represent main targets of drugs in the central nervous system. Interaction of drugs with these molecules induces a signaling cascade, which finally ends up with the control of ion channel conductance. Since the electric activity of single neurons depends on the set of momentarily active ion channels, communication between neurons is governed by channel activity. From here, it is obvious that electrical field potentials reflect the information of larger local networks of electrically active neurons, by representing the interaction of drugs with their targets within the concert of neurotransmission including complex modulation from feedback loops. Frequency analysis of the field potentials in the presence of drugs leads to the so-called electropharmacogram, which has been widely used to characterize drug actions on rat and human brains. Comparison of the electropharmacogram of a research compositions can be made with the electropharmacograms of reference pharmaceuticals and botanicals, since similarity of electropharmacogram between research composition and reference compound indicates similarity in CNS activity, and enables understanding of health applications in humans. Dimpfel, W. 2015. Drug Discovery and Translational Medicine. Freienbrink Herstellung und Verlag. ISBN: 978-3-7386-7039-4, pp. 47-54.

Increased alpha waves (8-12.99 Hz) in humans, as during meditation for example, indicate a reduction of stress and anxiety, and that the brain is relaxed. Beta waves (13-29.99 Hz) range from 13-20 Hz during daily activity (beta-1 waves), while the presence of high-frequency (waves (beta-2 and beta-3 waves) indicates stress, excessive concentration, and anger. Thus, a composition that stimulates alpha waves and short wavelength beta-1 waves, while stimulating beta-2 waves to a lesser extent, is expected to relieve stress and anxiety.

CNS stimulants have been found to influence brain wave activity. It is well known in the art that the attenuation or stimulation pattern and type of brain wave activity reflects underlying brain activities including attention and depression. The anatomical location of the activity can also be related to specific brain functions, for example activation of memory through activation of the hippocampus. Sleepiness and/or fatigue, for example, have been shown to be correlated to a significant increase of alpha wave activity and a decrease of gamma wave activity. Papadelis et al., *Proceedings of the 28th IEEE EMBS Annual International Conference*, New York City, USA, Aug. 30-Sep. 3, 2006, pp. 6201-6204. Increased gamma-band EEG activity is associated with states of high arousal, alertness, or attention. Attenuation of alpha- and beta-activity in the in-vivo EEG from implanted brain electrodes generally correlate to an increase in neurotransmission, resulting in increased alertness, stimulation and anti-depressant effects. The midbrain dopamine center comprises a key network for reward, salience, motivation, and mood and decreased serotonin metabolism and functioning in the central nervous system is associated with depression. Specific neurotransmitter release can be related to antidepressant and anti-anxiety effect, as shown for serotonin-dopamine activity modulating drugs like Brexpiprazole or the serotonin and norepinephrine reuptake inhibitor (SNRI) ZBH2012001.

Differences in brain wave activities might be related to diseases like Obese Binge-Eating (BE). Subjects show greater frontal electrical beta brain wave activity in EEG results than the non-BE subjects during food presentation, while no significant differences between the groups were found in alpha, delta or theta amplitudes. This suggests that elevated frontal beta activity may be a marker of dysfunctional disinhibition-inhibition mechanism, which could make the obese BE women more vulnerable or sensitive to food and the environmental cues (Tammela et al., *Clin. Physiol. Funct. Imaging.*, 2010, Vol. 30, pp. 135-40). Thus, a composition that suppresses frontal electrical beta brain wave activity may act to suppress desire for excessive food.

Smoking cessation and nicotine withdrawal seems to affect brain wave activity, and nicotine deprivation among smokers can be associated with lesser resting cortical activity (i.e., greater power density in theta and alpha-1 EEG bands, which can be interpreted as reduction of noradrenalinergic and serotonergic activity, and lesser power in beta bands, related to an increase of glutamatergic/GABAergic neurotransmission). Comparison of low-frequency theta and alpha-1 waves during nicotine deprivation and satiation states showed that they were greater in the very low nicotine (deprivation) state relative to higher nicotine (satiation) condition, while no differences in the alpha-2, beta-1, and beta-2 bands were shown. Similarly, increased theta-wave activity was found in smokers who had abstained from smoking; administration of nicotine gum led to a reduction in theta-wave activity. Similarly, the alpha-1/alpha-2 ratio was elevated in smokers who had abstained from smoking, administration of nicotine gum led to a reduction in alpha-1/alpha-2 ratio. Elevated theta-wave activity and an elevated alpha-1/alpha-2 ratio in cortical activity may be indicative of withdrawal-related cognitive deficits. A composition that suppresses slow wave brain wave activity, e.g., theta and/or alpha-1 wave brain wave activity, or elevates alpha-2 activity relative to alpha-1 activity, may act to suppress the effects of nicotine withdrawal, and help a user reduce or stop smoking.

The present disclosure provides compositions useful for: reducing craving and appetite (mainly craving and appetite for calories dense sweet or fatty foods, sweet beverages and confections, and craving for smoking); prolonging the duration of satiety after eating; reducing appetite; reducing weight gain after smoking-cessation, and reducing relapse rate after smoking. Simultaneously these compositions improve mood, and act as anti-depressants, and thereby countering the severe mood side effects of craving and appetite reducing products like Rimonabant. The compositions disclosed herein reduce craving and appetite for calorie-dense foods, snacks and beverages, reduce craving for smoking, and do not cause nervousness, anxiety or depression, offers a CNS-activating effect and serve to maintain health and prolong healthspan and lifespan by promoting calorie restriction from reduced craving for calorie-dense foods, snacks, sweet beverages and confections, and reduced craving for cigarettes in smokers, and reduced craving for alcohol.

The compositions disclosed herein provide reduced appetite and craving, enhanced satiety, decreased stress, and increased mood over a relatively extended period of time, but are substantially free of side effects and have no addictive potential, so they can be consumed over a long period of time by any person or mammal.

The compositions disclosed herein may be included in food and beverage products including snack bars, chewing gum, confections, meal-replacement shakes, smoothies, beverages, chocolate and energy-drinks used for anti-craving, and enhanced satiety purposes to:

a) support a responsible and healthy weight management program of reduced calorie intake and regular exercise without the known negative side effect of existing appetite-reducing or satiety enhancing drugs and supplements; and b) support smoke cessation programs by reducing cravings for nicotine, while reducing the related side effects like depression, low mood, and weight gain.

Metabolic Health

Tigernuts have been shown in animal models to improve serum lipid profiles and reduce elevated serum glucose, while mangiferin has been shown to prevent hyperglycemia, and have antihyperlipidemic and antiatherogenic activities. These activities of the compositions further contribute to health, wellness, healthy ageing, and longevity.

The foregoing objects and advantages of the invention are illustrative of those that can be achieved by the various exemplary embodiments and are not intended to be exhaustive or limiting of the possible advantages that can be realized. Thus, these and other objects and advantages of the various exemplary embodiments will be apparent from the description herein or can be learned from practicing the various exemplary embodiments, both as embodied herein or as modified in view of any variation that may be apparent to those skilled in the art. Accordingly, the present invention resides in the novel methods, arrangements, combinations, and improvements herein shown and described in various exemplary embodiments.

SUMMARY

In light of the present need for effective anti-craving and satiety-enhancing products with mood enhancing and anti-depressive effects, a brief summary of various disclosed embodiments is presented. Such anti-craving and satiety enhancing products are needed to assist people involved in responsible weight management programs, in maintaining their weight after losing weight in a weight management program, or preventing weight gain after quitting smoking. Such anti-craving and appetite reducing products are required to aid and support people in reaching their goals, without the side effects of depression, weight gain, or relapse after the end of the program. Some simplifications and omissions may be made in the following summary, which is intended to highlight and introduce some aspects of the disclosed subject matter, but not to limit the scope of the invention. Detailed descriptions of preferred embodiments, adequate to allow those of ordinary skill in the art to make and use the inventive concepts, will follow in later sections.

Various embodiments disclosed herein relate to a combination of two natural products for decreasing craving, reducing appetite, enhancing satiety, and stress reduction and mood improvement, containing an extract of *Cyperus esculentus* and Mangiferin. The combination has an effect comparable to the appetite-reducing effect provided by either Rimonabant or Methylphenidate, but does not possess the negative drawbacks of these drugs. In addition, it has the capacity to enhance mood and reduce stress, as opposed to the increase in stress and low mood or depression commonly associated with weight-loss and smoke-cessation programs, and with the relapses seen commonly after completion of such programs. This combination is based on functional foods and is not addictive. It can be combined with numerous natural compounds or plant extracts for additional benefits or flavoring or can be added into existing formats, formulations and food products in several ways, being for example a liquid or a powder, granules, a gum or a sachet.

The ingredients of the described invention are a water or ethanolic extract of whole Tigernut or Tigernut peel, and pure mangiferin or a plant extract standardized to mangiferin, derived by extraction of, for example, mango leaves, mango bark, mango fruit, or honey bush tea. These products can form part of different products and can be combined in different ratios and added to other ingredients.

Various embodiments disclosed herein relate to methods for reducing craving, reducing appetite, and enhancing satiety to avoid weight-gain and relapse after smoking-cessation, improve mood and reduce stress and depression in a person in need thereof, by administering an herbal composition to said person. The herbal composition may comprise an effective amount of an extract of *Cyperus esculentus* peel, *Cyperus esculentus* rhizomes, or a combination thereof. In some embodiments, the herbal composition may comprise an effective amount of mangiferin, norathyriol, or an extract comprising mangiferin or norathyriol. In other embodiments, the herbal composition may comprise a mixture of an effective amount of an extract of *Cyperus esculentus* peel, *Cyperus esculentus* rhizomes, or a combination thereof; and an effective amount of mangiferin, norathyriol, or an extract comprising mangiferin or norathyriol.

In various embodiments, the extract of *Cyperus esculentus* peel and/or *Cyperus esculentus* rhizomes, or a combination thereof is an aqueous extract, an alcoholic extract, or a hydroalcoholic extract. The extract of *Cyperus esculentus* may be a hydroalcoholic extract of peel of *Cyperus esculentus* rhizomes. The extract of *Cyperus esculentus* peel and/or *Cyperus esculentus* rhizomes may be used in an amount of between 20 mg and 20 g per dose.

In various embodiments, the herbal composition contains mangiferin, norathyriol, or an extract comprising mangiferin or norathyriol, used in an amount of between 20 mg and 5 g per dose. In some embodiments, the herbal composition contains an extract comprising mangiferin or norathyriol in an amount sufficient to provide between 20 mg and 5 g mangiferin or norathyriol per dose. The extract comprising mangiferin or norathyriol may be a mangiferin-containing extract of a plant species in a genus selected from the group consisting of *Mangifera, Salacia, Cyclopia, Hypericum, Canscora, Fagraea, Gentiana, Hoppea, Swertia, Hypericum, Polygala, Zizyphus, Coffea*, and mixtures thereof.

Various embodiments disclosed herein relate to methods for reducing craving, reducing appetite, enhancing satiety, reducing stress and enhancing mood in a person or animal in need thereof, by administering a herbal composition to said person, by administering a mixture of an effective amount of:
   a) an extract of *Cyperus esculentus* peel, *Cyperus esculentus* rhizomes, or a combination thereof; and
   b) an effective amount of mangiferin or an extract comprising mangiferin, where the ratio of (a) to (b) is between about 1:1 and about 50:1, about 1:1 and 30:1, about 2:1 and 25:1, about 1:1 and 20:1, about 4:1 and 15:1, about 10:1 and 15:1, or about 12:1. In various embodiments, the effective amount of (a) is between 20 mg and 20 g per dose; and the effective amount of said mangiferin or said mangiferin-containing extract is between 5 mg and 5 g per dose. In some embodiments, the mixture of (a) and (b) is provided as a unit dose containing between about 10 mg and about 20 g per dose.

In various embodiments, the herbal compositions disclosed herein contain:
   a) a herbal composition comprising:
      i. an extract of *Cyperus esculentus* peel, *Cyperus esculentus* rhizomes, or a combination thereof;
      ii. an effective amount of mangiferin or an extract comprising mangiferin; or
      iii. a mixture of (i) and (ii); in combination with:
   b) an active ingredient to support weight management or smoking cessation activity selected from the group consisting of 5-hydroxytryptophan, B group vitamins, caffeine, celastrol, citicoline, citrulline, choline, chromium picolinate, coenzyme Q10, curcumin, docosahexaenoic acid, eicosapentaenoic acid, ginsenosides, glycomacropeptide, huperzine, hydrocycitrate, L-carnitine, L-carnosine, L-tryptophan, luteolin, ibogaine, magnesium, N-methyltyramine, oleamide, omega-3 fatty acids, octopamine, phenylalanine, phenylethylamine, phosphatidlyserine, phosphatidlyserine, quercetin, raspberry ketones, rutin, resveratrol, synephrine, taurine, taxifoline, theanine, theobromine, withaferin A, xanthohumol, yangonin, yohimbine, ecdysteroids (20HE), extracts of Aphanizomenon flos aqua and other blue-green algae, *Ascophyllum nodosum, Chlorella* and other microalgae, extracts of plant species of the genera *Abelmoschus, Acacia, Acnistus, Adansonia, Aframomum, Aloysia, Alpinia, Amaranthus, Amorphophallus, Anacardium, Arachis, Astragalus, Bacopa, Cajanus, Capsicum, Carraluma, Celastrus, Chicorium, Cinnamomum, Ciser, Cissus, Crocus, Centella, Citrus, Coca, Cola, Curcuma, Coffea, Celastrus, Camellia, Eleutherococcus, Ephedra, Euterpe, Garcinia, Ginkgo, Ganoderma, Glycyrrhiza, Griffonia, Gymnema, Hibiscus, Hoodia, Hordeum, Icarine, Ilex, Ipomoea, Irvingia, Kaempferia, Moringa, Murraya, Ocimum, Olea, Oreganum, Oryza, Paullinia, Panax, Persea, Phaseolus, Pinus, Prunus, Pfaffia, Piper Pueraria, Punica, Rhodiola, Rhaponticum, Shisandra, Sida, Sideritis, Simondia, Solanum, Tabernanthe, Tamarindus, Theobroma, Tragaopogon, Trichocaulon, Trigonella, Tripterygium, Vicia, Vigna, Vitis, Withania, Zingiber, Zizyphus*, resistant starch, the non-starch polysaccharides, including galactamannan, guar gum, locust bean gum, tara gum, ispaghula, β-glucans, konjacglucomannan, methylcellulose, gum tragacanth, detarium, plant and animal based proteins, hydrolysed proteins, and mixtures thereof.

Various embodiments disclosed herein relate to compositions and methods for reducing craving, reducing appetite, enhancing satiety while elevating mood, treating depression, and decreasing stress. Low mood and depression are common side effects of pharmaceuticals for reducing appetite and increasing satiety. The method comprises replacement of drugs for satiety and appetite reduction with a product of the composition comprising:
   a) an effective amount of an extract of *Cyperus esculentus* peel, *Cyperus esculentus* rhizomes, or a combination thereof, where the effective amount may be between about 20 mg and about 20,000 mg, between about 100 mg and about 5000 mg, between about 500 mg and about 4000 mg, or between about 1000 mg and about 3000 mg of the extract;
   b) an effective amount of mangiferin, norathyriol, or an extract comprising mangiferin or norathyriol, where the effective amount may be between about 10 mg and about 500 mg, between about 10 mg and about 350 mg, between about 10 and about 200 mg, between about 5 and about 150 mg, or between about 8 and about 100 mg of the extract; or
   c) a synergistic mixture of (a) and (b).

Various embodiments disclosed herein relate to methods for reducing craving, reducing appetite, enhancing satiety while enhancing mood and decreasing stress, preventing weight gain during and subsequent to smoking cessation, during responsible calorie restriction diets for maintaining health, facilitating healthy ageing and longevity of a composition comprising:
   a) an effective amount of an extract of *Cyperus esculentus* peel, *Cyperus esculentus* rhizomes, or a combination thereof, where the effective amount may be between about 20 mg and about 20,000 mg, between about 100 mg and about 5000 mg, between about 500 mg and about 4000 mg, or between about 1000 mg and about 3000 mg of the extract;
   b) an effective amount of mangiferin, norathyriol, or an extract comprising mangiferin or norathyriol, where the effective amount may be between about 10 mg and about 500 mg, between about 10 mg and about 350 mg, between about 10 and about 200 mg, between about 5 and about 150 mg, or between about 8 and about 120 mg of the extract; or
   c) a synergistic mixture of (a) and (b).

Either or both of *Cyperus esculentus* and mangiferin can be used to reduce craving, reduce appetite, and enhance satiety alone or in combination with a weight loss product or program or a smoking cessation program. Both extracts are anticipated, through their mood-activating effect to have mood-enhancing and anti-depressant activities comparable to Selegiline and other antidepressants. These extracts are expected to reduce craving as effectively as Rimonabant or Methylphenidate. However, these natural functional food extracts have been demonstrated to lack the undesirable side effects associated with the Rimonabant and Methylphenidate.

The combination of *Cyperus esculentus* and mangiferin leads to a reduction of craving, reduction of appetite, and enhanced satiety for food and reduction of craving for tobacco and nicotine, a reduction of depression and stress, and improved mood. This is unexpected, as usually products for reduction of appetite lead to depression, as seen with Rimonabant.

The combination of *Cyperus esculentus* and mangiferin has an EEG signature that is comparable to that of the pharmaceutical selegiline, which has an anti-depressant effect. The EEG signature in rats shows synergy for alpha-1 brain wave attenuation in vivo from implanted electrodes in rats, which indicates synergy of the composition for enhancing mood/treating depression, and decreasing stress.

Various embodiments disclosed herein relate to a method for reducing cravings for nicotine-containing products, and alcohol in a person attempting to quit smoking or reduce caloric intake, comprising administering a composition to the person, where the composition comprises:
a) an effective amount of an extract of *Cyperus esculentus* peel, *Cyperus esculentus* rhizomes, or a combination thereof;
b) an effective amount of mangiferin, norathyriol, or an extract comprising mangiferin or norathyriol; or
c) a synergistic combination of (a) and (b).

When the composition is administered to a person attempting to quit smoking, the composition is administered in an amount effective to reduce at least one of theta brain wave activity and an alpha-1/alpha-2 ratio in the person.

When the composition is administered to a person attempting to reduce caloric intake, the composition is administered in an amount effective to reduce cravings for food by reducing beta brain wave activity in the person.

When the composition is administered to a person attempting to quit smoking, the composition may be administered in an amount effective to:
reduce at least one of theta brain wave activity and an alpha-1/alpha-2 ratio in the person; and
reduce cravings for food and avoid weight gain by said persons by also reducing beta brain wave activity in said person.

Various embodiments disclosed herein relate to a method for reducing stress and improving mood in a human subject or person, comprising administering a composition to the person where the composition comprises:
a) an effective amount of an extract of *Cyperus esculentus* peel, *Cyperus esculentus* rhizomes, or a combination thereof;
b) an effective amount of mangiferin, norathyriol, or an extract comprising mangiferin or norathyriol; or
c) a synergistic combination of (a) and (b);
wherein said composition is administered in an amount effective to modulate alpha brain wave activity in said person. In various embodiments, the person is subject to stress from attempts to lose weight, control food intake, or stop smoking. The *Cyperus esculentus* extract/mangiferin composition helps relieve this stress by modulating alpha brain wave activity. Reduced stress may avoid relapses into eating or smoking.

BRIEF DESCRIPTION OF THE DRAWINGS

In order to better understand various exemplary embodiments, reference is made to the accompanying drawings, wherein.

DETAILED DESCRIPTION

The current application relates to herbal compositions for reducing craving and improving mood and depression/stress in a person in need thereof, comprising administering a composition to said person, where the composition comprises:
a) an effective amount of an extract of *Cyperus esculentus*;
b) an effective amount of mangiferin, norathyriol, or an extract comprising mangiferin or norathyriol; or
c) a synergistic combination of (a) and (b).

In the current application, the term "about" encompasses normal variability in the recited amounts. In the context of an effective amount of a biologically active ingredient, the term "about" means that the actual amount of a dosage form is between 80% and 125%, between 90% and 110%, or between 95% and 105% of a stated value. In the context of a ratio between biologically active ingredients, the term "about" means±20%, ±10%, or ±5% of the stated value.

In the current application, the term "a person in need thereof" refers to any person or human subject in need of craving reduction to support a weight management or anti-smoking program or in need of a mood enhancer and anti-depressant. Such personor human subjects may be children, adolescents, adults, or elderly persons. Such personor human subjects may be people with overweight, obesity or smokers in need of reduced craving while avoiding depression or improving their mood during and after a weight-loss or smoking-cessation program, thereby increasing adherence and reducing risk of relapse.

Various embodiments disclosed herein relate to herbal compositions for reducing craving and improving mood, comprising an effective amount of an extract of *Cyperus esculentus*. The extract of *Cyperus esculentus* may be an extract of the entire plant, or of any plant part. The plant part of *Cyperus esculentus* to be extracted may be the leaf, peel, root, rhizome, stem, tuber, or a combination thereof. The extract of *Cyperus esculentus* may be an extract of *Cyperus esculentus* peel, *Cyperus esculentus* rhizomes, a peel derived from *Cyperus esculentus* rhizomes, or a combination thereof. The plant part of *Cyperus esculentus* may be extracted with water, an organic solvent, or a mixture thereof. The organic extraction solvent may be a polar aprotic solvent, such as DMSO, acetone, or a mixture thereof; or a polar protic solvent, such as a lower alcohol having from 1 to 4 carbon atoms. In various embodiments, the extract of *Cyperus esculentus* is an extract of *Cyperus esculentus* peel, *Cyperus esculentus* rhizomes, a peel derived from *Cyperus esculentus* rhizomes, or a combination thereof, derived by extraction with water, a lower alcohol having from 1 to 4 carbon atoms, or a mixture thereof. In some embodiments, the extract of *Cyperus esculentus* is an extract of *Cyperus esculentus* peel, *Cyperus esculentus* rhizomes, a peel derived from *Cyperus esculentus* rhizomes, derived by extraction with a hydroalcoholic mixture of water and ethanol. The extract may be obtained from extraction by subcritical or supercritical CO2.

Various embodiments disclosed herein relate to herbal compositions for reducing craving and improving mood, comprising mangiferin or norathyriol. Mangiferin has a structure of formula Ia, where R is a 1,5-anhydro-D-glucitol ring. Norathyriol is an aglycone of mangiferin, and has a structure of formula Ib, where R is hydroxyl. Unless otherwise stated, the term mangiferin is here defined as encompassing:
  mangiferin as a pure compound, where "pure" is defined as meaning the compound is at least 90% mangiferin, at least 95% mangiferin, at least 98% mangiferin, or at least 99.5% mangiferin; or
  a composition comprising at least 90% by weight of a mixture of mangiferin and norathyriol.

Ia: R = 1,5-anhydro-D-glucitol
Ib: R = ——OH

Mangiferin is a xanthonoid polyphenol. Mangiferin is found in several botanicals, including extracts of mango fruit, mango peel, mango bark, and/or mango leaf, as well as in extracts of various Cyclopia species, e.g., Honeybush tea, and extracts of species in the genus Salacia. Mangiferin has acetyl cholinesterase inhibiting activity, an activity useful in improving cognitive function in Alzheimer's disease.

Mangiferin, a xanthonoid, is a natural phenolic compound formed from the xanthone backbone. If we refer to Mangiferin, its aglycone norathyriol is always included as an alternative ingredient. Mangiferin is an antioxidant and anti-inflammatory that exhibits various pharmacological activities, including anti-diabetic, anti-cancer, and anti-oxidant effects as well as anti-inflammatory, anti-viral, immunomodulatory and anti-microbial activities. Prevention of stress-induced effects related to neurodegenerative diseases, reduction of neurological brain deficits and a positive effect on injured neurons has been reported with mangiferin, indicating that Mangiferin may play a role in pathologies related to neuroinflammation and oxidative damage. Mangiferin may also enhance recognition memory and improve memory deficits, while the inhibition of $MAO_A$ seems to be responsible for its anti-depressant-like effect. No effects indicating a reduction of craving have been described in the literature Mangiferin of the invention may be extracted from a plant containing Mangiferin. Excellent sources of the desired material are *Mangifera indica* (fruit, bark or leaf) or Honey bush tea, which are preferably standardized to a concentration of 20-70% Mangiferin, depending on the raw material. However, mangiferin can be obtained from other sources, including plant species of the genera *Mangifera, Salacia, Cyclopia, Hypericum, Mangifera, Canscora, Fagraea, Gentiana, Hoppea, Swertia, Hypericum, Polygala, Zizyphus,* and *Coffea.*

Tigernut (*Cyperus esculentus*), a crop of the sedge family widespread across the world, is a typical Spanish food found on markets and in the supermarket. In Spain, the milky extract of Tigernut (i.e., "horchata de chufa"), a non-alcoholic beverage, has an annual economic impact of 60 million Euro. Tigernut is rich in fiber, proteins, sugars, oleic acid and glucose, as well as in phosphorus, potassium, and vitamins C and E. Tigernut is useful for enhancing blood circulation, preventing heart disease, and reducing the risk of colon cancer. The scientific literature has not described any effect of chufa toward reduction of cravings, e.g., cravings for food or tobacco, or improvement of mood.

Whole Tigernut and Tigernut peel aqueous and 30% ethanolic extracts contain high amounts of fat and carbohydrates, but no detectable alkaloids or flavonoids. The extracts have a very pleasant and sweet taste, so that no restriction due to taste has to be made. Oral ingestion of 4 g of Tigernut extract provides a reduction of craving as well as a calming effect.

Figure 1:
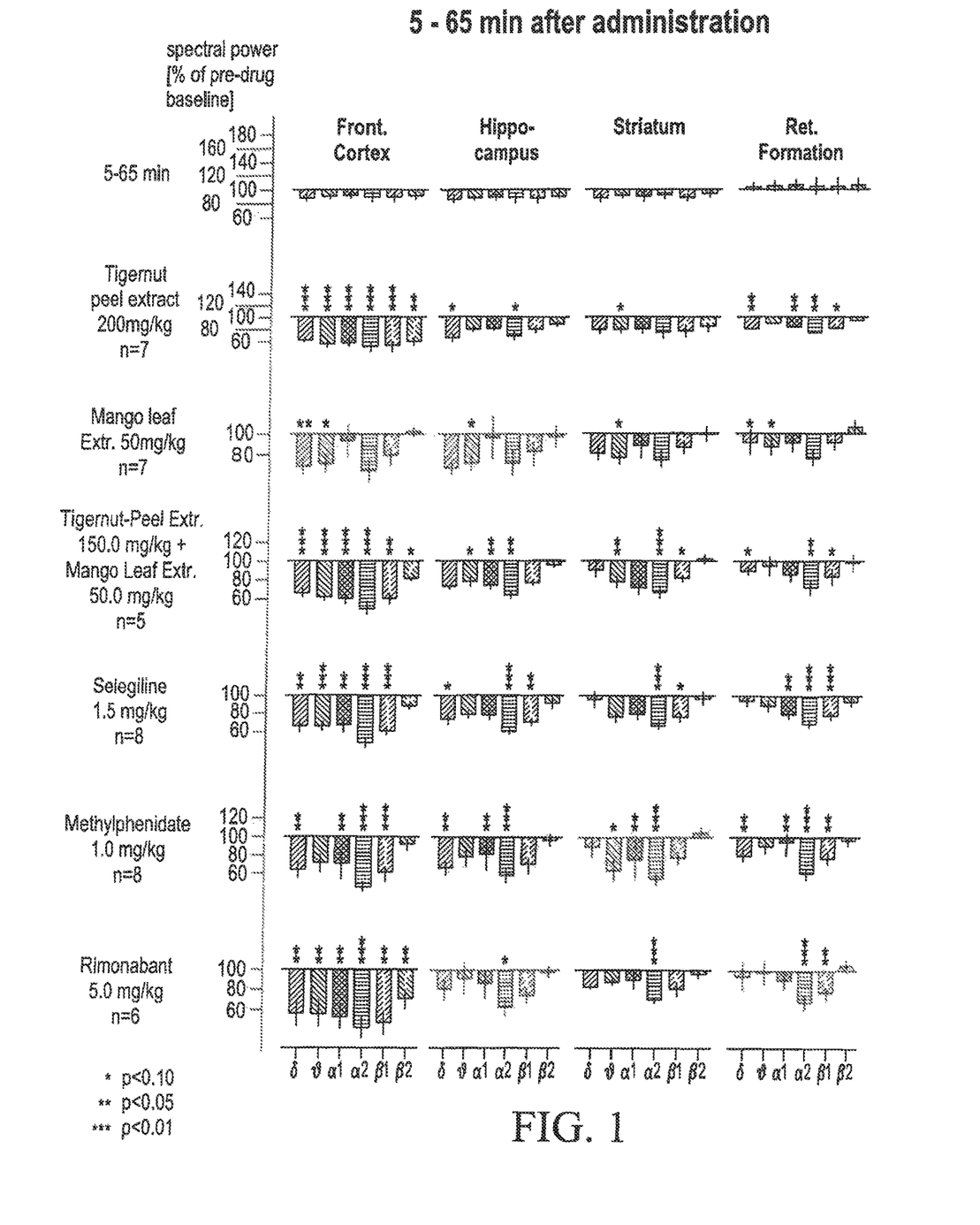
FIG. 1 shows encephalographic (EEG) studies on *Cyperus esculentus* tuberous rhizome extracts, Mango leaf extract, *Cyperus esculentus* tuberous rhizome extracts plus mango leaf extract, Rimonabant, Methylphenidate, and Selegiline, where statistical significance is designated as follows: *=$p<0.10$, =$p<0.05$, *=$p<0.01$.

It has now been found in accordance with the present invention that the combination of Tigernut and Mangiferin serves to moderate the bitter taste and unusual flavor of Mangiferin. Furthermore, the electropharmacogram of the combination is strikingly similar to the electropharmacograms of Rimonabant and Methylphenidate (Ritalin), both appetite inhibitors, and Selegiline (an antidepressant drug and anti-Parkinson's drug successfully used for smoking-cessation and as anti-depressant) (FIG. 1). Further, the invention resulted in a synergistic attenuation of Hippocampus alpha 1 and alpha 2 brain waves in rats (FIG. 2D), representing an activation of the neurotransmitters serotonin and dopamine, which are closely related to the reward system and the homeostasis of regulation of food intake.

Mangiferin and its aglycone metabolite norathyriol may be included in the disclosed compositions as pure compounds, or as components of an extract of a plant species in a genus selected from the group consisting of *Mangifera*, Salacia, Cyclopia, *Hypericum, Canscora, Fagraea, Gentiana*, Hoppea, Swertia, *Hypericum*, Polygala, Zizyphus, *Coffea* and mixtures thereof. The plant species contain mangiferin and/or norathyriol, and may be extracted with water, an aqueous base, a polar protic organic solvent, a polar aprotic organic solvent, or a mixture thereof. In various embodiments, the plant species comprises mangiferin, and is extracted with water, a lower alcohol having 1 to 4 carbon atoms, or a mixture thereof.

In various embodiments, the herbal composition contains mangiferin, norathyriol, or an extract comprising mangiferin or norathyriol, used in an amount of between 20 mg and 5 g per dose. The herbal composition may contain an extract comprising mangiferin or norathyriol of between 20 mg and 5 g per dose. If the concentration of mangiferin and/or norathyriol in the extract is known, the extract may be provided in an amount sufficient to provide between 20 mg and 5 g mangiferin or norathyriol per dose. Thus, for example, if an extract of a plant of the genus *Mangifera* contains 30% mangiferin, the extract may be provided in an amount of between 20 mg and 5 g per dose, based on the weight of the extract. Alternatively, the *Mangifera* extract may be administered in an amount of between 66.7 mg and 16.7 grams per dose, so as to provide between 20 mg and 5 g mangiferin per dose.

Various disclosed embodiments relate to herbal compositions containing Chufa or Tigernut extracts and mangiferin-containing botanical extracts, where the compositions are effective in enhancing CNS activity in the frontal cortex, hippocampus and striatum. In various embodiments, the compositions are effective for reduction of cravings, as shown by increased alpha wave activity in the brain. The compositions are also effective for improving mood and reducing depression, as shown by the similarity to Selegiline and the increased release of Serotonin, indicated by reduction of alpha-1 waves in rat EEG.

Through animal encephalographic (EEG) studies, the current application demonstrates that Chufa or Tigernut extracts (prepared by extraction of *Cyperus esculentus* tuberous rhizome) and mangiferin (as pure compound) and mangiferin-containing botanical extracts are strikingly similar in CNS profile to each other. Further, they are surprisingly similar in activity to the known appetite reducer Rimonaband and Methylphenidate. Chufa extracts are less potent than mangiferin. In a human adult subject, about 4 grams of chufa extract has about the same activity as about 400 mg mangiferin.

The key discoveries presented herein are that *Cyperus esculentus* extracts and mangiferin have a very similar CNS activating effect (as evidenced by EEG) to each other and to Rimonabant, Methylphenidate and Selegiline. However, unlike Rimonabant, *Cyperus esculentus* extracts and mangiferin also exhibit a calming, de-stressing activity when ingested. Further, *Cyperus esculentus* extracts and mangiferin exhibit a plateau effect. Beyond a certain threshold value, an increased intake of these extracts does not give greater CNS stimulation, minimizing abuse potential. Even at high servings or doses, *Cyperus esculentus* extracts and mangiferin exhibit none of the well-known side effects, e.g., sleeplessness and depression, caused by excessive doses of Rimonabant or Methylphenidate.

Chufa peels have, in the prior art, generally been considered to be a waste product of Chufa processing. However, it has been discovered that a 30% ethanol-water extract of chufa peels, e.g., peels of Chufa tuberous rhizomes, exhibit more potent activating activity than a 30% ethanol-water extract of whole chufa, which in turn has more potent activity than a water extract of whole chufa. Ethanolic, aqueous, and hydroalcoholic extracts of Chufa tuberous rhizomes all, however, exhibit desirable CNS activating activity.

In various embodiments, Chufa or Tigernut extracts and mangiferin-containing botanical extracts may be taken as individual active ingredients. Chufa or Tigernut extracts are desirably taken by an adult human in an amount of about 0.1 g/day to about 10 g/day, about 0.5 g/day to about 8 g/day, about 1 g/day to about 5 g/day, or about 1 g/day to about 4 g/day. Mangiferin-containing botanical extracts are desirably taken by an adult human in an amount of about 25 mg/day to about 5 g/day, about 50 mg/day to about 2 g/day, about 100 mg/day to about 1 g/day, or about 200 mg/day to about 400 mg/day.

Chufa or Tigernut extracts and mangiferin-containing botanical extracts have synergistic activity on alpha-1 and alpha-2 brain wave activity in the hippocampus. The increase in alpha wave activity in the Hippocampus, comparable to that of Rimonabant and Methylphenidate, is evidence that the composition increases anti-craving effect. Chufa or Tigernut extracts and mangiferin-containing botanical extracts are desirably combined in a ratio of between about 0.5:1 and about 30:1, about 1:1 and about 20:1, about 5:1 and about 10:1 and about 7.5:1.

Chufa or Tigernut extracts and mangiferin-containing botanical extracts, whether taken separately or together, have a rapid onset of action. Within an hour after oral ingestion, or within 15-20 minutes after buccal mucosal absorption, EEG results show an impact of the extracts on neural activity. The extracts have a long duration of action, of between 3-6 hours. When Chufa or Tigernut extracts and mangiferin-containing botanical extracts are combined and ingested together, the duration of action is at least 5 hours, and the effect of the combination on brain wave activity after 5 hours is significantly greater than the effect on brain wave activity of either extract individually 5 hours after ingestion.

Persons who have ingested Chufa or Tigernut extracts and mangiferin-containing botanical extracts as disclosed herein, taken individually or together, report that the extracts reduce craving. Persons who have ingested Chufa or Tigernut extracts and mangiferin-containing botanical extracts as disclosed herein, taken individually or together, report that the extracts improves motivation, and elevates mood, while simultaneously inducing a feeling of calm, reduced anxiety, and reduced stress, tension and nervousness, and reduced impulsivity. Unlike Rimonabant, even at very high doses the extracts do not cause low mood, depression or increase of suicidal risk.

Chufa or Tigernut extracts and mangiferin-containing botanical extracts as disclosed herein are not bitter, taste pleasant, and are perfectly suited to application in functional foods and beverages. The extracts can be used to reduce craving and improve mood in foods, beverages, and supplements without causing depression or anxiety. As discussed above, the herbal compositions disclosed herein contain a herbal composition comprising:

an extract of *Cyperus esculentus* peel, *Cyperus esculentus* rhizomes, or a combination thereof;

an effective amount of mangiferin or an extract comprising mangiferin; or a mixture of an extract of *Cyperus esculentus* peel or rhizomes and mangiferin or an extract comprising mangiferin.

The claimed compositions may comprise:
i) from about 10% to about 95% by weight, about 25% to about 90% by weight, about 40% to about 85% by weight, or about 50% to about 80% by weight, of an extract of *Cyperus esculentus* peel, *Cyperus esculentus* rhizomes, or a combination thereof; and from about 5% to about 90% by weight, about 10% to about 75% by weight, about 15% to about 60% by weight, or about 20% to about 50% by weight of a further ingredient for enhancing mood or decreasing stress or anxiety;
ii) from about 10% to about 95% by weight, about 25% to about 90% by weight, about 40% to about 85% by weight, or about 50% to about 80% by weight, of mangiferin or an extract comprising mangiferin; and from about 5% to about 90% by weight, about 10% to about 75% by weight, about 15% to about 60% by weight, or about 20% to about 50% by weight of the further ingredient for enhancing mood or decreasing stress or anxiety; or
iii) from about 10% to about 95% by weight, about 25% to about 90% by weight, about 40% to about 85% by weight, or about 50% to about 80% by weight, of a mixture of
   a. an extract of *Cyperus esculentus* peel and/or rhizomes and b. mangiferin or an extract comprising mangiferin; and
from about 5% to about 90% by weight, about 10% to about 75% by weight, about 15% to about 60% by weight, or about 20% to about 50% by weight of the further ingredient for enhancing mood or decreasing stress or anxiety.

c) This further ingredient for further enhancing mood or decreasing depression, stress or anxiety is selected from the group consisting of 5-hydroxytryptophan, B group vitamins, caffeine, citicoline, citrulline, choline, chromium picolinate, coenzyme Q10, curcumin, glycomacropeptide, huperzine, hydrocycitrate, L-carnitine, L-carnosine, L-tryptophan, luteolin, ibogaine, magnesium, N-methyltyramine, oleamide, omega-3 fatty acids, octopamine, phenylalanine, phenylethylamine, phosphatidlyserine, phosphatidlyserine, quercetin, raspberry ketones, rutin, resveratrol, synephrine, taurine, taxifoline, theanine, theobromine, xanthohumol, yangonin, yohimbine, ecdysteroids (20HE), extracts of Aphanizomenon flos aqua and other blue-green algae, *Ascophyllum nodosum, Chlorella* and other microalgae, extracts of plant species of the genera *Aframomum, Aloysia, Alpinia, Astragalus, Bacopa, Capsicum, Carraluma, Chicorium, Cinnamomum, Ciser, Cissus, Crocus, Centella, Citrus, Coca, Cola, Curcuma, Coffea, Celastrus, Camellia, Eleutherococcus, Ephedra, Euterpe, Garcinia, Ginkgo, Ganoderma, Glycyrrhiza, Griffonia, Gymnema, Hoodia, Hordeum, Hypericum, Icarine, Ilex, Ipomoea, Irvingia, Kaempferia, Ocimum, Olea, Oreganum, Paullinia, Panax, Persea, Phaseolus, Pinus, Prunus, Pfaffia, Piper Pueraria, Punica, Rhodiola, Rhaponticum, Shisandra, Sida, Sideritis, Simondia, Solanum, Tabernanthe, Tamarindus, Theobroma, Tragaopogon, Trichocaulon, Trigonella, Vicia, Vigna, Vitis, Withania, Zingiber, Zizyphus*, the non-starch polysaccharides, including galactamannan, guar gum, locust bean gum, tara gum, ispaghula, β-glucans, konjac glucomannan, methylcellulose, gum tragacanth, detarium, and mixtures thereof.

Mangiferin and *Mangifera* extracts may be incorporated into an oral dosage form, including an orally dissolvable or dispersible buccal strip, a chewing gum, a tablet, a capsule, an emulsion, a suspension, an oral spray, effervescent, dissolvable granules or powder, a sachet, or a clear beverage. Chufa extracts, alone or in combination with Mangiferin and *Mangifera* extracts, are typically opaque and milky in beverage form, and may be incorporated into an oral dosage form, including an orally dissolvable or dispersible buccal strip, a chewing gum, a tablet, a capsule, dissolvable granules or powder, a sachet, an emulsion, a suspension, dairy milk, non-dairy milks, yoghurt, and milk-fruit juice combinations.

The compositions disclosed herein may be provided as:
an orally dissolvable or dispersible buccal strip for mucosal absorption, a chewing gum, a chewable tablet, a lozenge, an effervescent tablet, a capsule, or an emulsion;
a functional chocolate, marzipan, or sweetmeat,
a functional spread in measured doses in a foil sachet, to be spread on bread or crackers;
a powder with a measuring spoon for addition to any beverage or food;
a lozenge;
an oral or nasal spray;
a non-dairy creamer in sachet or stick form to add to a beverage; and
a snack-bar, candy, or cookie.

The compositions disclosed herein may be used for anti-craving reasons in weight control programs of for smoking cessation and may be added to all kind of formats, replacing pharmaceuticals currently used for appetite reduction or satiety.

However, it also loses the harmful side effects of Rimonabant, including depression and risk of suicide. Removing all or part of the pharmaceutical drug in a product with an extract of *Cyperus esculentus* peel and/or rhizomes, mangiferin or an extract comprising mangiferin, or a mixture thereof allows the side effects of this drug (for example Rimonabant) to be removed, while restoring the desired CNS stimulant activity. It is estimated that about 2 grams chufa extract is equivalent to 10 mg Rimonabant or 10 mg Methylphenidate. Similarly, Mangiferin and mangiferin-containing extracts may be used to reduce craving in a food, beverage or supplement. It is estimated that about 100 to about 200 mg mangiferin is equivalent to 10 mg Rimonabant or 10 mg Methylphenidate.

A composition combining *Cyperus esculentus* extract and Mangiferin in a ratio of between about 20:1 and 1:1 may be used instead of 10 mg Rimonabant or 10 mg Methylphenidate. From about 20 mg to about 200 mg of the *Cyperus esculentus* extract/Mangiferin combination may be used to replace 10 mg of Rimonabant or 10 mg Methylphenidate. The combined *Cyperus esculentus*-mangiferin or mangiferin containing plant extract is used in an amount of between 10 mg and 20 g for Rimonabant or Methylphenidate substitution.

The *Cyperus esculentus* extract/Mangiferin composition in accordance with the invention may be a simple mixture of the two ingredients after the extraction process. The invention may advantageously include additional ingredients with the purpose to further increase the craving reducing effect and the positive effect on weight loss or smoking cessation. Therefore, it may be advantageous to add, for example, other appetite reducing, mood improving, anti-obesity, or anti-craving components to the combined product presented, to enhance the anti-craving effect provided by the present invention. The same products can also be added to *Cyperus esculentus* extract or Mangiferin separately.

To improve other aspects of the invention, as for example the effect on mood and well-being, natural products like *Ganoderma, Garcinia Kola* and *Astragalus* can be combined with the composition. Ingredients enhancing absorption and bioavailability may be added, like Piperin, Capsaicin or Ginger. Natural and artificial sweeteners, and flavors such as coffee, vanilla, hazelnut, chocolate, cream, or fruit flavor can be integrated. Nutrients like omega-3 fatty acids, vitamins and minerals may be added. For athletes, adaptogens including Withania and *Rhodiola*, products improving muscle health and recovery like the amino acids citrulline and phosphatidlyserine, natural nitrate sources including spinach and beetroot, anabolic or anti-catabolic components like ecdysterones and ursolic acid, and antioxidants may be added. Suitable antioxidants include polyphenols with anti-oxidant or xanthin-oxidase inhibitory effects can be added. Representative polyphenols include catechins from Green tea, polyphenols from Cocoa, resveratrol from grape, *Polygonum* or Gnetum gnemon seeds, xanthohumol from *Humulus lupulus*, and luteolin, rutin or quercetin.

The *Cyperus esculentus* extract/Mangiferin composition may be combined with anti-craving, weightloss or anti-smoking products such as Hoodia, *Curcuma* and Ginger, and/or mood improving-products such as Ginkgo, citicoline or huperzine.

The amount of the additional ingredient included in the in the composition of the present invention varies depending on the characteristics of each additional ingredient. The invention can be combined, for example, with an antioxidant in a ratio from 1:50 to 50:1.

The composition has a wide range of useful applications for the industry: it can be provided in a liquid, syrup, or solid (tablet) or pulverized or granulated or gum form or can be incorporated into food products of liquid, solid (tablet), syrup granulated or pulverized consistency. The liquid may be presented in a concentrated form to be diluted by mixing it with teas, coffee, water or milk, juices, yoghurts or smoothies to provide the final consumable liquid beverage providing the craving reduction typically associated with Rimonabant and the mood enhancing benefits. The concentration of the present invention varies depending on the product format, purpose and/or the additional ingredients.

The compositions disclosed herein may be used for replacing pharmaceuticals currently used for appetite reduction or satiety, notably Rimonabant and Methylphenidate. In certain embodiments, about 2 to 5 grams *Cyperus esculentus* extract has an activity which is equivalent to 5.5 to 14.5 mg Rimonabant or 5.5 to 14.5 mg Methylphenidate; about 3 to 4 grams *Cyperus esculentus* extract has an activity which is equivalent to 8.5 to 11.5 mg Rimonabant or 8.5 to 11.5 mg Methylphenidate; or about 3.5 grams *Cyperus esculentus* extract has an activity which is equivalent to 10 mg Rimonabant or 10 mg Methylphenidate. Similarly, about 100 to about 400 mg mangiferin is equivalent to about 10 to 40 mg Rimonabant or about 2 to 8 mg Methylphenidate; about 200 to about 300 mg mangiferin is equivalent to about 20 to 30 mg Rimonabant or about 4 to 6 mg Methylphenidate; or about 250 mg mangiferin is equivalent to about 25 mg Rimonabant or 5 mg Methylphenidate.

A composition combining *Cyperus esculentus* extract and Mangiferin in a ratio of between about 20:1 and 1:1 may be used for reduction of cravings. From about 20 mg to about 200 mg of the *Cyperus esculentus* extract/Mangiferin combination may be used to replace 5 mg to 50 mg Rimonabant or 1 to 10 mg Methylphenidate; or about 100 mg of the *Cyperus esculentus* extract/Mangiferin combination may be used to replace 25 mg Rimonabant or 5 mg Methylphenidate. The combined *Cyperus esculentus*-mangiferin or mangiferin containing plant extract can be used in an amount of between 10 mg and 20 g for replacing 10 mg Rimonabant or 10 mg Methylphenidate substitution.

Example 1

Test Subjects:
Fisher 344 rats (11 months of age and day-night converted, weight about 350-400 g, provided by Charles River Laboratories, D-97633, Sulzfeld) were used in a series of experiments on the effects of various herbal and pharmaceutical products on central nervous system activity. Products were provided to the test subjects orally (gavage).

Test Substances:
The substances tested in this study included:
A control vehicle (0.9% NaCl);
*Cyperus esculentus* tuberous rhizome, ethanol extract, administered in an amount of 200 mg/kg to 7 rats;
Mango leaf, ethanol extract, administered in an amount of 50 mg/kg to 7 rats;
*Cyperus Esculentus* tuberous rhizome peel, ethanol extract, 150 mg/kg, plus Mango leaf extract, containing 60% of Mangiferin, 50 mg/kg, administered to 5 rats
Selegiline, administered in amount of 1.5 mg/kg to 8 rats
Methylphenidate administered in an amount of 1.0 mg/kg to 8 rats
Rimonabant administered in amount of 5 mg/kg to 6 rats EEG signals were recorded by telemetry from 4 implanted electrodes in the frontal cortex, hippocampus and striatum of freely moving rats from inside a totally copper shielded room. Signals were collected in sweeps of 4-second duration and Fast Fourier transformed using a Hanning window. EEG signals were recorded over a period starting 5 minutes after administration of the test substances, and ending 65 minutes after administration of the test substances. Sampling frequency was 512 Hz. Spectra were averaged in steps of 3 minutes each and displayed on-line. In an off-line procedure, the spectra were averaged to give longer periods for further analysis and data presentation. Spectral activity within the frontal cortex, hippocampus, striatum and reticular formation was recorded. Oral administration of the control vehicle (0.9% NaCl) only resulted in minor changes of spectral power within the four brain areas.

Through these in vivo animal encephalographic (EEG) studies, it has surprisingly been discovered that *Cyperus esculentus* tuberous rhizome extracts, mangiferin, mangiferin-containing botanical extracts and the combination of *Cyperus esculentus* tuberous rhizome extract and mangiferin are not only strikingly similar in CNS profile to each other, but also surprisingly similar to reference Rimonabant, Methylphenidate, and Selegiline. As shown in FIG. 1, during the first hour of recording, each of these extracts or compounds provide a decrease in spectral power in the in vivo EEG in the frontal cortex, and some decrease of brain waves in hippocampus, striatum and reticular formation. Such decreases correlate to an activation of neurotransmission. As shown in FIG. 1, the main significant effect of Rimonabant, Methylphenidate and Selegiline on the neural activity in all brain areas is directed to alpha-2 (green) (p<0.01, relative to pre-drug baseline), related to dopaminergic neurotransmission. *Cyperus esculentus* tuberous rhizome extract and the combination of *Cyperus esculentus* tuberous rhizome extract and manogo leaf extract also have a strong impact on alpha 2 waves, similar to that of Rimonabant, Methylphenidate and Selegiline, a drug that increases blood dopamine levels and greatly improves depressive symptoms.

Administration of a mixture of *Cyperus esculentus* tuberous rhizome, 30% ethanol extract, and Mango leaf extract containing 60% Mangiferin decreased brain wave activity from delta, theta, alpha-1, alpha-2, beta-1, and beta-2 waves in the frontal cortex, the hippocampus, and the striatum. The effect on brain wave activity of the *Cyperus esculentus* extract/Mango leaf extract mixture was roughly similar to the effect on brain wave activity of 5.0 mg/kg Rimonabant, 1.0 mg/kg Methylphenidate, and 1.5 mg/kg Selegiline, as shown in FIG. 1.

Example 2

Test Subjects:
Fisher 344 rats (11 months of age and day-night converted, weight about 350-400 g, provided by Charles River Laboratories, D-97633, Sulzfeld) were used in further experiments on the effects of *Cyperus esculentus* tuberous rhizome, ethanol extract, and mangiferin on central nervous system activity. Products were provided to the test subjects orally (gavage).

Test Substances:

The substances tested in this study included:

A control vehicle (0.9% NaCl);

*Cyperus esculentus* tuberous rhizome peel, 30% ethanol extract, administered in an amount of 200 mg/kg to 7 rats Mango leaf extract containing 60% Mangiferin, administered in an amount of 50 mg/kg to 6 rats; and a mixture of *Cyperus esculentus* tuberous rhizome peel, 30% ethanol extract, in an amount of 150 mg/kg, and Mango leaf extract containing 60% Mangiferin, in an amount of 50 mg/kg, the combination being administered to 6 rats.

EEG signals were recorded by telemetry from 4 implanted electrodes in the frontal cortex, hippocampus and striatum of freely moving rats from inside a totally copper shielded room. EEG signals were recorded over:

a first period, starting 5 minutes after administration of the test substances, and ending 65 minutes after administration of the test substances; and a second period, starting 245 minutes (4.1 hours) after administration of the test substances, and ending 305 minutes (5.1 hours) after administration of the test substances.

Figure 2A:
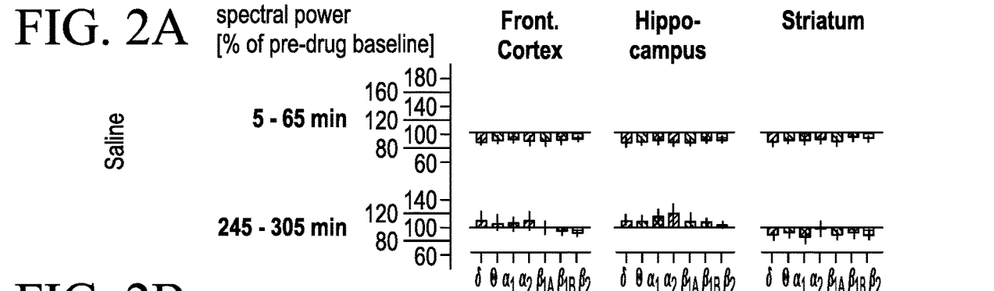
FIGS. 2A to 2D show the impact on the neural activity in the frontal cortex, hippocampus, and striatum of saline control (FIG. 2A), *Cyperus esculentus* tuberous rhizome, 30% ethanol extract (FIG. 2B), Mango leaf extract containing 60% Mangiferin (FIG. 2C) and a mixture of *Cyperus esculentus* tuberous rhizome, 30% ethanol extract, and Mango leaf extract containing 60% Mangiferin (FIG. 2D), where statistical significance is designated as follows: *=$p<0.10$, =$p<0.05$, *=$p<0.01$.
Figure 2B:
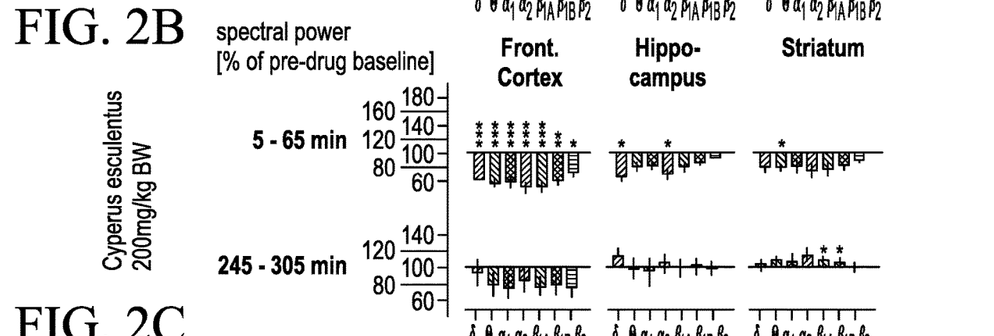

Neural Activity in the Frontal Cortex and Hippocampus:

Administration of a saline control had little impact on the neural activity in the frontal cortex and hippocampus, as shown in FIG. 2A. However, administration of *Cyperus esculentus* tuberous rhizome, 30% ethanol extract, significantly decreased brain wave activity in the frontal cortex. About an hour after administration of the *Cyperus esculentus* extract, brain wave activity in the frontal cortex from delta-, theta-, alpha-, and beta-waves decreased to, on average, about 60% of the pre-drug baseline, as shown in FIG. 2B. Simultaneously, delta and alpha-2 waves decreased significantly in the hippocampus ($p<0.1$). After about 5 hours, the effect on delta and alpha-2 waves in the hippocampus was no longer visible, although suppressed activity in the frontal cortex was still present.

Figure 2C:
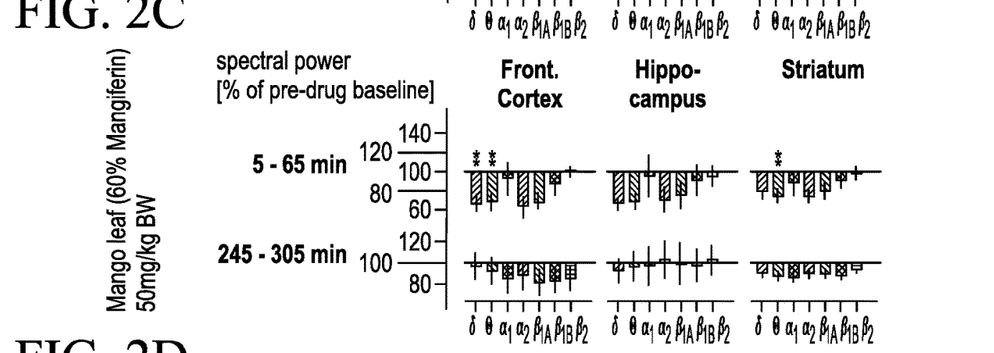

Administration of Mango leaf extract containing 60% Mangiferin also decreased brain wave activity in the frontal cortex. About an hour after administration of the Mango leaf extract, brain wave activity in both the frontal cortex and the hippocampus from delta, theta, alpha-2, and beta-1 waves decreased noticeably, as shown in FIG. 2C. The decrease in delta and theta wave activity was statistically significant ($p<0.05$). After about 5 hours, there was no significant change in brain wave activity in the hippocampus or in delta and theta waves in the frontal cortex, relative to the pre-drug baseline, although suppressed activity in alpha and beta waves in the frontal cortex was present.

Figure 2D:
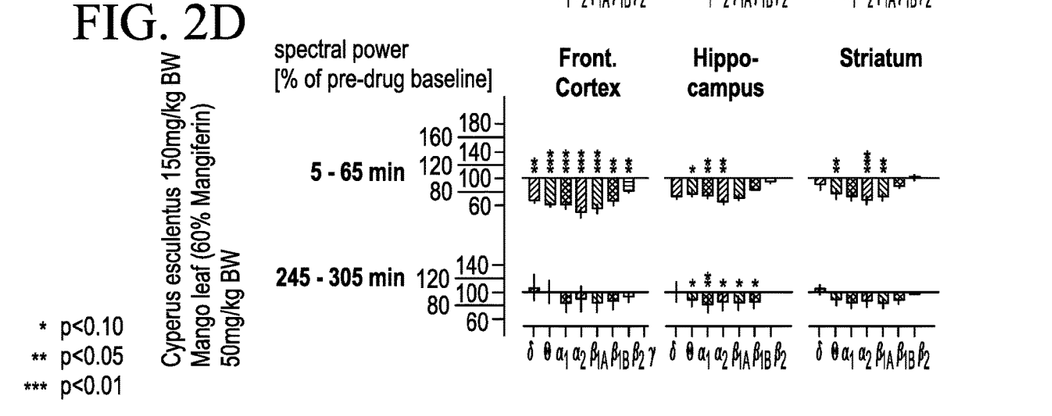

Administration of a mixture of *Cyperus esculentus* tuberous rhizome peel, 30% ethanol extract, and Mango leaf extract containing 60% Mangiferin decreased brain wave activity in the frontal cortex to roughly the same extent as *Cyperus esculentus* tuberous rhizome, 30% ethanol extract, alone. About an hour after administration of combined extracts, brain wave activity in the frontal cortex and the hippocampus from delta, theta, alpha-1, alpha-2, and beta-1 waves decreased significantly ($p<0.01$), as shown in FIG. 2D. The effect on alpha-2 waves was greater than the effect on alpha-1 waves, as seen in FIG. 2D; this leads to a reduction in alpha-1/alpha-2 ratio. Based on the change in theta-wave activity and in alpha-1/alpha-2 ratio, the *Cyperus esculentus* extract/Mango leaf extract combination has potential for aiding smokers who wish to stop smoking.

Simultaneously, brain wave activity in the hippocampus from theta, alpha-1, and alpha-2 waves decreased significantly ($p<0.05$ for alpha-1 and alpha-2 waves; $p<0.1$ for theta waves).

After about 5 hours, there was no significant change in brain wave activity from theta, alpha-1, alpha-2, beta-1, and beta-2 waves in the frontal cortex, relative to the pre-drug baseline, although suppression of brain wave activity in the hippocampus was present. In the hippocampus, suppression of activity from theta, alpha-1, alpha-2, beta-1, and beta-2 waves was observed ($p<0.05$ for alpha-1 waves; $p<0.1$ for theta, alpha-2, beta-1, and beta-2 waves). Additionally, relative to the saline control, the *Cyperus esculentus* alone, and the Mango leaf extract alone, the combination of the *Cyperus esculentus* and the Mango leaf extract produced a statistically significant ($p<0.05$) increase in gamma wave activity in the frontal cortex. Increased gamma-band EEG activity is associated with states of alertness or attention.

Synergism is observed in brain wave activity in the hippocampus upon administration of a mixture of *Cyperus esculentus* tuberous rhizome peel, 30% ethanol extract, and Mango leaf extract containing 60% Mangiferin. First, neither the *Cyperus esculentus* extract nor the Mango leaf extract has a statistically significant impact on alpha-1 brain wave activity in the hippocampus, either in the first hour after administration or 5 hours after administration, as shown in FIGS. 2B and 2C. However, the combination of *Cyperus esculentus* extract and the Mango leaf extract has a statistically significant impact on alpha-1 brain wave activity in the hippocampus, both in the first hour after administration and 5 hours after administration ($p<0.05$, both 1 hour after administration and 5 hours after administration). Further, neither the *Cyperus esculentus* extract nor the Mango leaf extract has any statistically significant impact on brain wave activity in the hippocampus 5 hours after administration, as shown in FIGS. 2B and 2C. The combination of *Cyperus esculentus* extract and the Mango leaf extract has a synergistic, statistically significant impact on alpha-brain wave activity in the hippocampus 5 hours after administration, related to an increase of serotonergic activity.

In summation, the effect of the combination of Tigernut extract nor Mango leaf extract can be explained through the significant, synergistic and long-lasting decrease of alpha-1 brain wave activity in the rats, representing an activation of serotonergic and dopaminergic neurotransmission, measured in the hippocampus during the first hour and during the fifth hour after intake. Neither Tigernut extract nor Mango leaf extract (60% Mangiferin) or pure Mangiferin administered alone showed a significant decrease of alpha-1 brain wave activity at these time periods (see FIG. 2). As discussed above, a decrease of alpha-1 brain wave activity from implanted electrodes in the rat is the result of increased serotonergic and dopaminergic neurotransmission. Such a change in neurotransmission, if measured by external EEG electrodes in a person, would be observed as an increase in alpha-1 brain wave activity. In both rats and humans, increased serotonergic and dopaminergic neurotransmission correlates with increased relaxation and reduced stress.

Example 4: Human Studies

Four-Week Study

Four adults participated in a 4 week observational study, taking:

3 grams of a 30% ethanol extract of *Cyperus esculentus* tuberous rhizome, one to two times daily for a week, 400 mg of a mango leaf extract containing 284 mg of mangiferin, taken once daily for a week, and a combination of 3 grams of the *Cyperus esculentus* tuberous rhizome extract and 400 mg mango leaf extract (300 mg Mangiferin), taken once to twice daily for two weeks.

The subjects made self-reported notes in diaries on side effects, well-being, mood, concentration, alertness, stress. No side effects were experienced. All of the subjects noted distinctly improved mood and well-being and a reduction of cravings for food and enhanced satiety that lasted from 2 to 4 hours after ingestion of the *Cyperus esculentus* tuberous rhizome extract, the mango leaf extract, and the combination of the mango leaf extract and tigernut extract. Two individuals missed lunchtime on several days as the usual feeling of hunger at a precise hour didn't come up. *Cyperus exculentus* is less strong than mango leaf extract, therefor a higher dose was needed for the same effect.

In two adult subjects mango leaf extract and *Cyperus esculentus* were formulated into gelatin gummies and into chewing gum to check for buccal absorption. In both subjects, for both formulations, there was a marked effect on reducing craving, and reducing appetite.

Two-Week Study

In a 2-week observational study where 9 adults ingested a combination of 3 grams of the *Cyperus esculentus* tuberous rhizome extract and 400 mg mango leaf extract daily over a two week period, seven participants (78%) felt less hungry at lunch time and could delay lunch without problems for 30 minutes to one hour Addictive Potential In a study where 6 adults ingested a combination of 3 grams of the *Cyperus esculentus* tuberous rhizome extract and 400 mg mango leaf extract daily over a two-week period, no signs of dependence or tolerance were noted, and there was no evidence of physical or psychological withdrawal. In a similar study where 2 adults ingested a combination of 3 grams of the *Cyperus esculentus* tuberous rhizome extract and 400 mg mango leaf extract daily over a two-month period, no signs of tolerance, dependence or withdrawal were observed. Further, daily intake over 2 months did not show any negative side effects, but improved mood and well-being were noted.

Two human subjects ingested larger doses of intake of the *Cyperus esculentus* tuberous rhizome/mango leaf extract in high doses (up to 20 g/day); increasing the dosage did not increase the observed effect on mood and craving.

Profile of Mood States

In a double blind, randomized, placebo-controlled 2-armed study with a parallel design with 32 adults subjects the Profile of Mood States (POMS) questionnaire was completed an hour after a single oral dose of a composition of the invention containing Tigernut extract (1000 mg) and mangiferin (300 mg) from a mango leaf extract, and for placebo.

The Profile of Mood States is a psychological rating scale used to assess transient, distinct mood states. The assessment provides a rapid method of assessing transient, fluctuating active mood states. It is an instrument for measuring and monitoring treatment change in clinical, medical, and addiction treatment centers. It is also well suited to clinical drug trials because its sensitivity to change allows accurate documentation of the effects of drugs on mood state. POMS is a standard validated psychological test containing 65 words or statements describing feelings that people have. The test requires an indication, for each word or statement, how the subject has been feeling in the previous week, Possible scores for each word or statement include:
 a) Score 1: Dejection;
 b) Score 2: Sullenness;
 c) Score 3: Fatigue; and
 d) Score 4: Thirst for action.

The results of the four scores are presented in the following table:

| | | Profile of Mood States (POMS) | | | |
|---|---|---|---|---|---|
| | | Score 1 Dejection | Score 2 Sulleness | Score 3 Fatigue | Score 4 Thirst for action |
| Placebo n = 16 | Mean: | 0.24 | 0.38 | 0.73 | 2.84 |
| Tigernuts-mangiferin n = 16 | Mean: | 0.08 | 0.13 | 0.59 | 3.18 |

The results showed that only an hour after ingestion of the Tigernuts-mangiferin combination, the 3 POMS scores for negative states of mind (dejection, sullenness, fatigue) all decreased compared to the placebo, while the POMS score for the positive state of mind, thirst for action, increased in score for the composition compared to placebo.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A method for reducing cravings for at least one of calorie dense food, sweetened beverages, and confections in a person in need thereof, comprising administering an effective amount of a composition to said person,
 said composition comprising:
 a) a first composition comprising an extract of *Cyperus esculentus* peel, *Cyperus esculentus* rhizomes, or a combination thereof; and
 b) a second composition comprising mangiferin or an extract comprising mangiferin;
  wherein the first and second compositions are administered in a ratio such that, in the hippocampus, a change in alpha and beta-1 wave activity is increased, relative to a change in alpha and beta-1 wave activity from administration of either the first composition or the second composition individually.

2. The method according to claim 1, wherein said composition is administered in an amount effective to reduce theta brain wave activity and alpha-1/alpha-2 ratio in said person.

3. The method according to claim 1, wherein said person is attempting to reduce caloric intake; and
 said method reduces cravings for food in said person;
 wherein said composition is administered in an amount effective to reduce beta brain wave activity in said person.

4. The method according to claim 1, wherein said method further reduces cravings for food in said person; wherein said composition is administered in an amount effective to reduce theta brain wave activity, beta brain wave activity, and alpha-1/alpha-2 ratio in said person.

5. The method according to claim 1, wherein said extract of *Cyperus esculentus* peel, *Cyperus esculentus* rhizomes, or a combination thereof is an aqueous extract, an alcoholic extract, or a hydroalcoholic extract, or a subcritical or supercritical CO2 extract.

6. The method according to claim 1, wherein said effective amount of said *Cyperus esculentus* peel, *Cyperus esculentus* rhizomes, or a combination thereof is between 20 mg and 20 g per dose.

7. The method according to claim 1, wherein said effective amount of said mangiferin is between 20 mg and 5 g per dose.

8. The method according to claim 1, wherein said effective amount of said extract comprising mangiferin is sufficient to provide between 20 mg and 5 g mangiferin per dose.

9. The method according to claim 1, wherein said extract comprising mangiferin is a mangiferin-containing extract of a plant species in a genus selected from the group consisting of *Mangifera*, Salacia, Cyclopia, *Hypericum, Canscora, Fagraea, Gentiana*, Hoppea, Swertia, *Hypericum*, Polygala, Zizyphus, and mixtures thereof.

10. The method according to claim 1, wherein (a) is an aqueous extract, an alcoholic extract, or a hydroalcoholic extract of *Cyperus esculentus* peel, *Cyperus esculentus* rhizomes, or a combination thereof.

11. The method according to claim 1, wherein (b) comprises mangiferin or a mangiferin-containing extract of a plant species in a genus selected from the group consisting of *Mangifera*, Salacia, Cyclopia, *Hypericum, Canscora, Fagraea, Gentiana*, Hoppea, Swertia, *Hypericum*, Polygala, Zizyphus, and mixtures thereof.

12. The method according to claim 1, wherein the ratio of (a) to (b) is between about 1:1 and about 50:1.

13. The method according to claim 1, wherein the ratio of (a) to (b) is between about 1:1 and about 20:1.

14. The method according to claim 1, wherein the ratio of (a) to (b) is between about 4:1 and about 15:1.

15. The method according to claim 10, wherein said effective amount of (a) is between 20 mg and 20 g per dose; and said effective amount of said mangiferin or said mangiferin-containing extract is between 5 mg and 5 g per dose.

16. The method according to claim 12, wherein said composition is provided as a unit dose containing between 10 mg and 20 g per dose.

17. The method according to claim 1, wherein said composition further comprises an active ingredient selected from the group consisting of 5-hydroxytryptophan, B group vitamins, caffeine, citicoline, citrulline, choline, chromium picolinate, coenzyme Q10, curcumin, glycomacropeptide, huperzine, hydrocycitrate, L-carnitine, L-carnosine, L-tryptophan, luteolin, ibogaine, magnesium, N-methyltyramine, oleamide, omega-3 fatty acids, octopamine, phenylalanine, phenylethylamine, phosphatidlyserine, phosphatidlyserine, quercetin, raspberry ketones, rutin, resveratrol, synephrine, taurine, taxifoline, theanine, theobromine, xanthohumol, yangonin, yohimbine, ecdysteroids (20HE), extracts of Aphanizomenon flos aqua and other blue-green algae, *Ascophyllum nodosum, Chlorella* and other microalgae, extracts of plant species of the genera Aframomum, Aloysia, Alpinia, *Astragalus, Bacopa, Capsicum*, Carraluma, Chicorium, *Cinnamomum*, Ciser, Cissus, *Crocus*, Centella, Citrus, Coca, Cola, *Curcuma, Coffea, Celastrus, Camellia*, Eleutherococcus, Ephedra, *Euterpe, Garcinia*, Ginkgo, *Ganoderma, Glycyrrhiza*, Griffonia, Gymnema, Hoodia, *Hordeum, Icarine, Ilex, Ipomoea*, Irvingia, Kaempferia, *Ocimum, Olea, Oreganum, Paullinia, Panax, Persea, Phaseolus, Pinus, Prunus*, Pfaffia, *Piper Pueraria, Punica, Rhodiola, Rhaponticum, Shisandra, Sida*, Sideritis, Simondia, *Solanum*, Tabernanthe, Tamarindus, *Theobroma*, Tragaopogon, Trichocaulon, *Trigonella, Vicia, Vigna, Vitis, Withania, Zingiber*, Zizyphus, the non-starch polysaccharides, including galactamannan, guar gum, locust bean gum, tara gum, ispaghula, β-glucans, konjacglucomannan, methylcellulose, gum tragacanth, detarium, and mixtures thereof.

\* \* \* \* \*